(12) United States Patent
James

(10) Patent No.: US 12,397,136 B2
(45) Date of Patent: Aug. 26, 2025

(54) BALLOON FOR EXPANDING AN ORIFICE

(71) Applicant: IPH001 Pty Ltd, Sydney (AU)

(72) Inventor: Andrew E. James, Sydney (AU)

(73) Assignee: IPH001 Pty Ltd, Sydney (AU)

( * ) Notice: Subject to any disclaimer, the term of this patent is extended or adjusted under 35 U.S.C. 154(b) by 507 days.

(21) Appl. No.: 17/617,260

(22) PCT Filed: Jun. 12, 2020

(86) PCT No.: PCT/AU2020/050597
§ 371 (c)(1),
(2) Date: Dec. 7, 2021

(87) PCT Pub. No.: WO2020/248021
PCT Pub. Date: Dec. 17, 2020

(65) Prior Publication Data
US 2022/0249812 A1    Aug. 11, 2022

(30) Foreign Application Priority Data

Jun. 13, 2019    (AU) .............................. 2019902063

(51) Int. Cl.
*A61M 25/10* (2013.01)
*A61B 90/00* (2016.01)
(Continued)

(52) U.S. Cl.
CPC ......... *A61M 25/1002* (2013.01); *A61B 90/02* (2016.02); *A61M 25/1029* (2013.01);
(Continued)

(58) Field of Classification Search
CPC .............. A61M 25/1002; A61M 90/02; A61M 2210/167; A61M 29/02;
(Continued)

(56) References Cited

U.S. PATENT DOCUMENTS 6,607,545 B2    8/2003   Kammerer et al.
9,393,142 B2    7/2016   Watts et al.
(Continued)

FOREIGN PATENT DOCUMENTS

AU    2009243931 B2    11/2013
CN       107497035 A    12/2017
(Continued)

OTHER PUBLICATIONS

International Search Report in PCT/AU2020/050597, mailed Jul. 23, 2020, 3 pages.
(Continued)

*Primary Examiner* — Kelly J Bekker
*Assistant Examiner* — Lindsey R. Rivers
(74) *Attorney, Agent, or Firm* — Kilpatrick Townsend & Stockton LLP

(57) ABSTRACT

A balloon is disclosed for expanding an orifice. The balloon comprises a hollow body having a head. The body is closed at a distal end and open at a proximal end. The head extends from the distal end. The balloon also comprises a hollow neck positioned between the open proximal end and the distal end of the body. In the balloon, a wall thickness of the neck is greater than a wall thickness of the head. In a variation, the balloon can be configured such that, when the balloon is inflated, the head expands in a radial direction greater than in the longitudinal direction and a diameter of the body remains approximately constant during inflation. Also disclosed is a system for expanding an orifice. The system includes such a balloon and an inflation device for inflating the balloon. Also disclosed is a kit comprising the system and a container. Further, disclosed is a mould and a method for forming the balloon.

15 Claims, 6 Drawing Sheets

(51) Int. Cl.
*A61M 29/02* (2006.01)
*B29C 45/26* (2006.01)
*A61B 17/00* (2006.01)
*B29K 83/00* (2006.01)
*B29L 31/00* (2006.01)

(52) U.S. Cl.
CPC ......... *A61M 29/02* (2013.01); *B29C 45/2616* (2013.01); *A61M 2207/10* (2013.01); *A61M 2210/167* (2013.01); *B29K 2083/00* (2013.01); *B29L 2031/753* (2013.01)

(58) Field of Classification Search
CPC .. A61M 2025/1059; A61M 2025/1084; A61M 25/1029; A61B 17/22032; A61B 17/42; A61B 17/4241; A61B 17/12022; A61B 17/12136; A61B 2017/4216; A61B 2017/4225; A61B 2017/00557; A61B 2017/00526; A61F 2005/415; B29C 45/2616; B29K 2083/00; B29L 2031/753
See application file for complete search history.

(56) References Cited

U.S. PATENT DOCUMENTS

| | | | |
|---|---|---|---|
| 2002/0082635 A1* | 6/2002 | Kammerer | A61M 25/1029 606/193 |
| 2003/0153940 A1 | 8/2003 | Martin et al. | |
| 2004/0098003 A1 | 5/2004 | Nishiki | |
| 2004/0127932 A1 | 7/2004 | Tilak et al. | |
| 2011/0166414 A1 | 7/2011 | Watts et al. | |
| 2011/0190867 A1 | 8/2011 | Vonderwalde et al. | |

FOREIGN PATENT DOCUMENTS

| | | | |
|---|---|---|---|
| DE | 19925156 | 8/2000 | |
| DE | 19925156 C1 * | 8/2000 | ............ A61M 29/02 |
| JP | 2001-524332 A | 12/2001 | |
| JP | 2004-202237 A | 7/2004 | |
| JP | 2009-509805 A | 3/2009 | |
| WO | 99/26857 A1 | 6/1999 | |
| WO | 2006/115537 A1 | 11/2006 | |
| WO | 2007/040441 A1 | 4/2007 | |

OTHER PUBLICATIONS

Examination Report in Indian Application No. 202117059806 mailed Oct. 26, 2022, 6 pages.
Extended European Search Report in EP20823609.1, mailed Oct. 2, 2023, 9 pages.
Hearing Notice in Indian Application No. 202117059806, Hearing Notice, mailed Feb. 12, 2025, 3 pages.

* cited by examiner

BALLOON FOR EXPANDING AN ORIFICE

TECHNICAL FIELD

This disclosure relates generally to balloons that are used to expand an orifice, such as a foreskin of a male subject.

BACKGROUND

Phimosis is a condition in which the male foreskin is unable to retract properly from the head of the penis (or glans) due to an unusually tight foreskin. Many males with the condition are born with it. Phimosis can also be caused by trauma, infection or autoimmune disease. Zipper trauma is a well-documented cause of phimosis, and Lichen sclerosis and Balanitis Xerotica Obliterans (BXO) are autoimmune diseases known to trigger phimosis.

Over time phimosis can also be exacerbated by tearing of the opening of the foreskin, resulting in scarring. Phimosis can result in a higher likelihood of infection, a build-up of smeg (the white substance under the foreskin), ballooning of the foreskin during urination, pain during sex and a loss of sensation during sex. A more serious condition, paraphimosis, occurs when a tight foreskin is pulled back over the head of the penis and remains there, constricting the blood flow. This can rapidly lead to permanent damage and/or loss of the penis.

Devices used to treat phimosis insert a balloon under the foreskin where the balloon is then gently inflated which causes the foreskin to stretch. This procedure is repeated over a course of a few days to a few months to treat phimosis. A problem with current balloons is that they do not always stay in the correct position under the foreskin and they do not always have reproducible inflation characteristics, which can make it difficult to provide consistent treatment for a patient.

It is to be understood that a reference herein to the prior art does not constitute an admission that the publication forms a part of the common general knowledge in the art, in Australia or any other country.

SUMMARY

The disclosure provides in a first aspect a balloon for expanding an orifice. The balloon comprises a hollow body having a head, the body being closed at a distal end and open at a proximal end, the head extending from the distal end. The balloon also comprises a hollow neck positioned between the open proximal end and the distal end of the body. A wall thickness of the neck is greater than a wall thickness of the head.

An advantage of having a wall thickness of the neck being greater than a wall thickness of the head is that the neck may not expand, or there may be substantially minimised expansion of the neck, when the balloon is inflated. This may help to ensure that the expansion of the head during inflation is approximately uniform, which can help to ensure an even pressure is applied to the orifice being expanded by the balloon. For example, when treating phimosis, the approximately uniform expansion of the balloon may apply even pressure to the foreskin. Approximate uniform expansion of the head of the balloon may also help to ensure that the balloon does not slip out of the orifice in use.

In an embodiment a wall thickness of the head at the distal end may be greater than the wall thickness of a remainder of the head. Having a wall thickness of the head at the distal end (e.g. a tip region/end of the head) being greater than the wall thickness of the remainder of the head may allow the balloon to expand in a radial direction more than a longitudinal direction extending from the proximal end to the distal end of the body during inflation. In some embodiments, the head may only expand in a radial direction during inflation i.e. the head of the balloon does not expand in the longitudinal direction. Limiting the expansion of the head to a radial direction may help to ensure that the balloon only exerts a radial force onto the orifice rather than a force in a longitudinal direction. For tissue such as the foreskin, minimising expansion in the longitudinal direction may help to prevent the balloon from being ejected out from under the foreskin during inflation.

In an embodiment, a first end of the neck may extend from the proximal end of the body to a second remote end of the neck. The first end of the neck may comprise a peripheral lip that protrudes outwardly therefrom. The neck may comprise a waist intermediate its first and second ends. A wall thickness of the waist may be less than a wall thickness of a remainder of the neck. The waist may be formed as a progressive narrowing of the wall thickness of a section of the neck. Having a waist may help to give the body some flexibility to allow the body to be removed from a mould during manufacture. The waist may also help to reduce the amount of material required to form the balloon.

An external diameter of the neck may be substantially constant for a length of the neck. The external diameter of the neck may range from about 5 mm to about 15 mm, such as about 10 mm. A portion of the neck may have an external diameter that is substantially constant, and another portion of the neck may have an external diameter that is not constant. The head may have a diameter ranging from about 6 mm to about 18 mm in a deflated state. The opening at the proximal end may have a diameter ranging from about 5 mm to about 10 mm. In an embodiment, the diameter of the opening is about 8 mm. The proximal end may be configured to fit onto an inflation device.

The disclosure provides in a second aspect a balloon for expanding an orifice. The balloon comprises a hollow body having a head, the body being closed at a distal end and open at a proximal end with a longitudinal axis extending therebetween. The head extends from the distal end. The balloon is configured such that when the balloon is inflated the head expands in a radial direction greater than in the longitudinal direction and a diameter of the body remains approximately constant during inflation.

A length of the balloon extending along the longitudinal direction may remain approximately constant during inflation. The body may define a neck that is positioned between the head and the proximal end. A diameter of the neck may remain substantially unchanged during inflation. The balloon of the second aspect may be otherwise as defined for the first aspect.

In an embodiment of the disclosure, the balloon may be formed from silicone. The body and head may be unitary with one another. The balloon may be self-supporting such that in a deflated state the balloon does not collapse in on itself. Having a self-supporting balloon may assist a user inserting the balloon into an orifice. For example, when the orifice is an ear, a self-supporting balloon may allow a user to insert the balloon into the ear irrespective of the patient's orientation, and when the orifice is the space between the foreskin and the head of a penis the self-supporting balloon may help with placement of the balloon under the foreskin.

The disclosure also provides in another aspect a system for expanding an orifice, comprising: a balloon as set forth above, and an inflation device for inflating the balloon.

The system may further comprise a flow regulator to regulate the flow of fluid into and out of the balloon. The flow regulator may be used to maintain the balloon in an inflated state. The system may further comprise a connector used to connect the balloon to the inflation device. The connector may function to clamp the proximal end to the balloon to the flow regulator.

The disclosure also provides in another aspect a kit comprising a system as set forth above, and a container for housing the system. The container may be a box. The box may be cardboard and/or plastic. The kit may include instructions for operating the system.

The disclosure also provides in another aspect a mould for forming a balloon that is used to expand an orifice. The balloon comprises a hollow body having a head, the body being closed at a distal end and open at a proximal end, and a hollow neck extending from the open proximal end of the body. The mould comprises a spigot having a first region for forming the body and a second region for forming the head. The first region has a first diameter and the second region has a second diameter, and the first diameter is less than the second diameter.

The spigot may further comprise a third region for forming a waist in the neck. The third region may have a third diameter that is less than the first diameter. The second region may comprise a recess that forms a part of the proximal end of the body. The mould may further comprise a female section for receiving the spigot. The female section may have a bore that has an internal diameter that is approximately constant. The balloon may be as set forth above. The spigot may be formed from two or more components that are connectable with one another to form the spigot.

Also disclosed is a method of forming a balloon, the balloon being used to expand an orifice. The method comprises: providing the mould as set forth above; applying a balloon precursor to the mould; and curing the balloon precursor to form the balloon.

The balloon precursor may be a silicone precursor material that is cured to form a silicone-based balloon. The method may further comprise a post-curing step to further cure the balloon. The balloon may be as set forth above.

BRIEF DESCRIPTION OF FIGURES

Embodiments will now be described by way of example only with reference to the accompanying non-limiting Figures, in which.

DETAILED DESCRIPTION OF EMBODIMENTS

Figure 1:
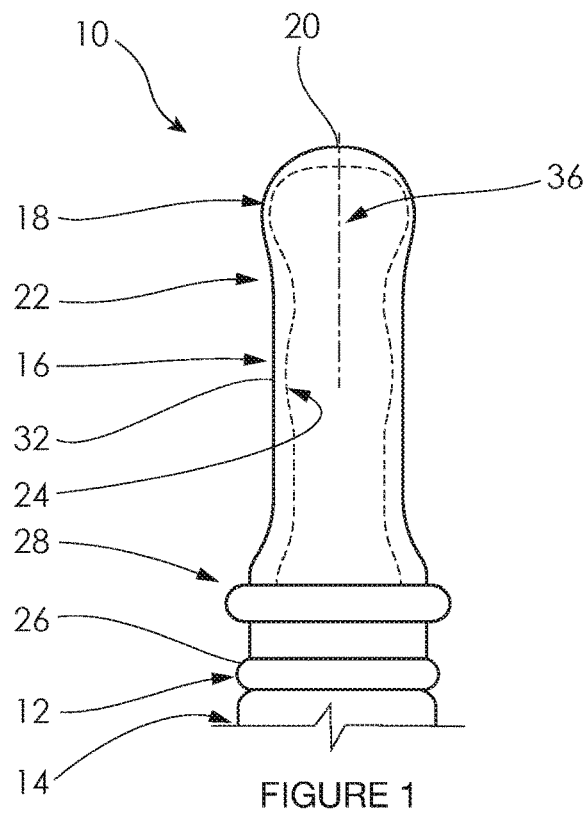
FIG. 1 is a side view of an embodiment of a balloon of the disclosure in a deflated state when mounted on a spigot.
Figure 2:
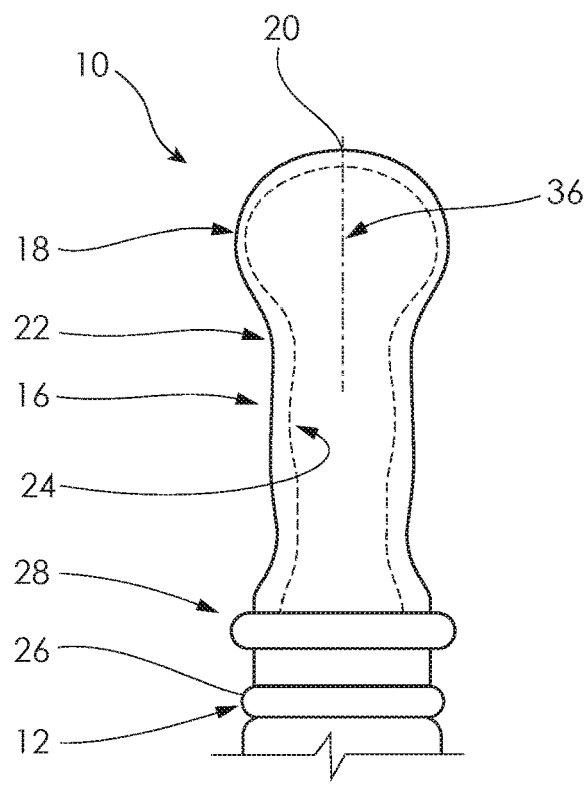
FIG. 2 is a side view of the balloon of FIG. 1 in an inflated state.
Figure 3:
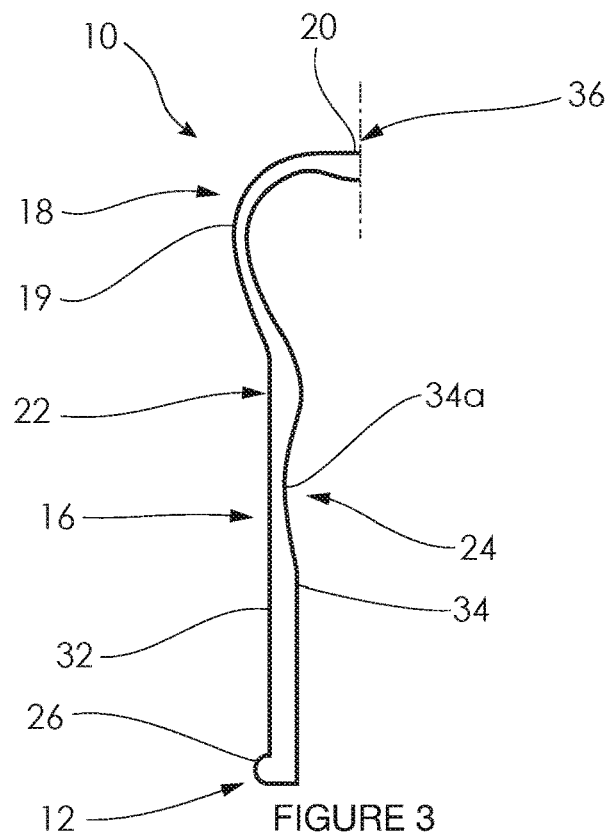
FIG. 3 shows a partial cross-section of an embodiment of a balloon.

Disclosed is a balloon for expanding an orifice. Referring to FIGS. 1 and 2, the balloon 10 has a hollow body in the form of hollow cylinder 16. The cylinder 16 has a proximal (first) end in the form of a base 12. Extending from the base 12 is a neck 22. The neck 22 is integrally formed with the cylinder 16. As best shown in FIG. 3, the cylinder 16 has an inner face 34 and an outer face 32. A diameter of the outer face 32 remains approximately constant from the base 12 to the neck 22. Extending from the neck 22 is a head 18. Terminating at a distal end (e.g. tip) of the balloon 10 is a tip region in the form of end 20. The neck 22 has a first end near (proximate) the base 12 and a second end remote (distal) from the base 12. Put simply, each end of the neck 22 is axially spaced apart from one another.

A lip in the form of resistance band 26 is positioned at the base 12 on the outer face 32. Resistance band 26 acts to apply a compressive force when the base 12 is sleeved over a fitting that is associated with an inflation device to prevent leakage of fluid when the balloon 10 is inflated with the fluid. In FIGS. 1 and 2 the fitting is in the form of spigot 14. An outer surface of the spigot 14 is in contact with the inner face 34 when the base 12 is sleeved over the spigot 14, and the resistance band 26 acts to compress the inner face 34 onto the outer surface of the spigot 14. A connector in the form of auxiliary ring 28 is also fitted over the cylinder 16 near the base 12 to compress the cylinder 16 onto the spigot 14. The spigot 14 can form part of a flow regulator. An auxiliary ring 28 acts as a clamp, such as a sable clamp, to apply a radially compressive force to the cylinder 16. The auxiliary ring 28 helps to ensure the base 12 of the balloon 10 remains attached to the spigot 14. However, the auxiliary ring 28 is not required in all embodiments, see for example FIG. 6 where the balloon 10 is mounted on the spigot without the auxiliary ring. Additionally, the resistance band 26 is not required in all embodiments.

The cylinder 16 has a waist positioned between the base 12 and the neck 22. In the embodiment shown in FIGS. 1 to 3, the waist is in the form of a channel or groove 24 that extends circumferentially around the inner face 34. The groove 24 has a depth that extends from the inner face 34 towards the outer face 32. The groove 24 is formed as a progressive narrowing of the wall thickness of the cylinder 16.

In the embodiment depicted in FIGS. 1 to 3, a wall thickness of the cylinder 16 near the base 12 is approximately similar to a wall thickness of the neck 22. In some embodiments the neck 22 has a wall thickness that is smaller or larger than the wall thickness of the cylinder near the base 12. Regardless of the wall thickness of the neck 22 and cylinder 16, a wall thickness of the groove 24, as defined by the narrowest thickness between the inner face at location 34a and outer face at location 32a, is less than the wall thickness of the base 12. The wall thickness of the groove 24 is also less than the wall thickness of the neck 22. The narrowest thickness between the inner face 34a and outer face 32a of the groove 24 is generally located at the maximum groove depth, for example at location 34a. The presence of groove 24 means that the neck 22 is defined by a circumferential projection that has a semi-hemispherical or curved cross-section that extends radially inwards. However, in embodiments where the groove 24 is positioned along the cylinder 16 at a location that is towards the base 12 more than the neck 22, the neck 22 may simply be defined by the end region of the cylinder 16. A wall thickness of the neck 22 is defined by the greatest distance between the inner face 34 and outer face 32. A longitudinal axis of the balloon 10 is represented by dashed line 36.

Figure 4:
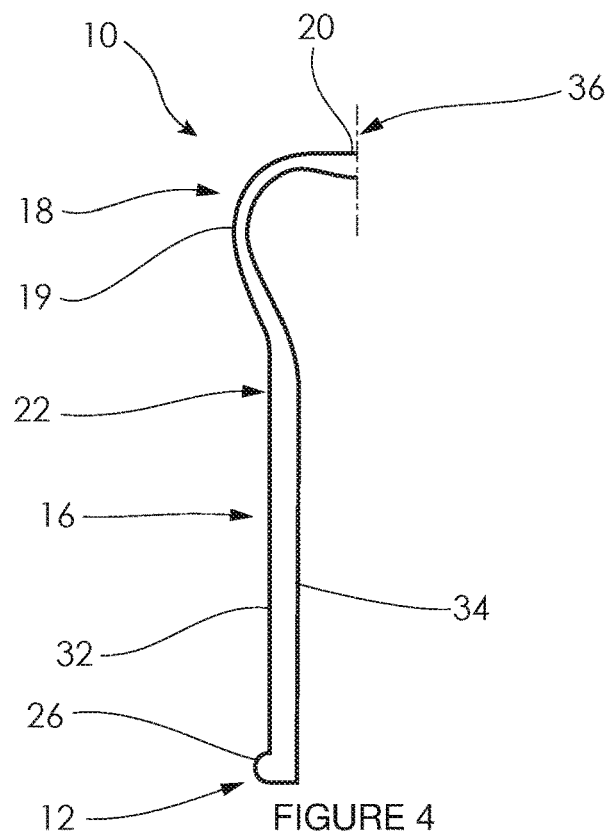
FIG. 4 shows a partial cross-section of another embodiment of a balloon.

The groove 24 is not required in all embodiments, and as shown in FIG. 4 the wall thickness of the cylinder 16 is constant from the base 12 to the neck 22.

In the embodiments shown in FIGS. 1-4 the head 18 has a bulbus (mushroom) shape. However, in an embodiment the head 18 is cylindrical and extends axially from the neck 22, as shown in FIG. 5.

The thickness of a sidewall portion 19 of the head 18 is less than the wall thickness at the neck 22. The end 20 of the head 18 has a wall thickness that is greater than the sidewall portion 19. The end 20 has a wall thickness that is generally less than the wall thickness of the neck 22, although in some embodiments the end 20 may have the same wall thickness as the neck 22. The transition from the neck 22 to the head 18 is provided as a progressive narrowing of the wall thickness of the cylinder 16 from the neck 22 to sidewall portion 19.

Specific dimensions of an embodiment of the balloon 10 in a deflated state (or uninflated state or non-expanded state) will now be described with reference to FIG. 5. It should be appreciated that the dimensions described in relation to the embodiment of FIG. 5 are exemplary only and are not intended to limit the dimensions of the balloon as set forth in this disclosure.

Figure 5:
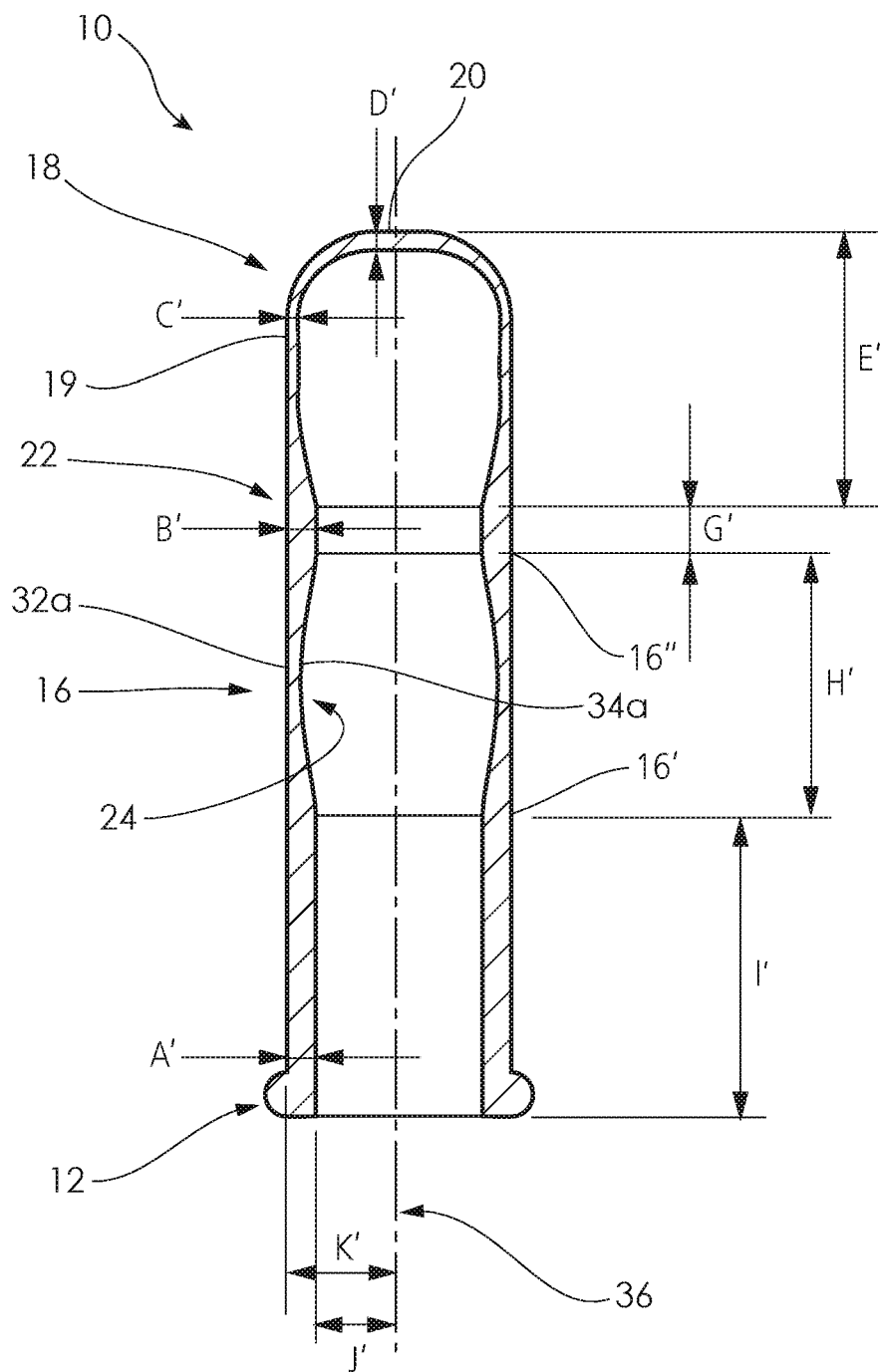
FIG. 5 shows a cross-section of another embodiment of a balloon

In the balloon shown in FIG. 5, the base 12 has a wall thickness A' that in one embodiment ranges from about 1.0 mm-2.0 mm, such as about 1.20 mm. In a specific embodiment, A' is 1.22 mm. The cylinder 16 has a wall thickness extending from the inner face 34a and outer face 32a ranging from about 0.3 mm-0.7 mm, such as about 0.50 mm. In a specific embodiment, a wall thickness extending from the inner face 34a to outer face 32a is 0.52 mm. The neck 22 has a wall thickness B' ranging from about 1.0 mm-2.0 mm, such as about 1.20 mm. In a specific embodiment B' is 1.21 mm. The sidewall portion 19 of the head 18 has a wall thickness C' ranging from about 0.2 mm-0.6 mm, such as about 0.3 mm-0.4 mm. In a specific embodiment C' is 0.35 mm. The end 20 has a wall thickness D' ranging from about 0.7 mm-1.1 mm, such as about 0.90 mm. In a specific embodiment D' is 0.89 mm.

Still referring to FIG. 5, a length I' from the base 12 to an intermediate point 16' of the cylinder 16 extending along an axial direction 36 of the balloon 10 ranges from about 10 mm-15 mm. In a specific embodiment the length I' is about 13.5 mm. A length H' from the intermediate point 16' to a distal end 16' of the cylinder 16 extending along the axial direction 36 of the balloon 10 ranges from about 10 mm-15 mm. In a specific embodiment length H' is about 12 mm. The neck 22 has a length G' extending along the axial direction 36 of the balloon 10 that ranges from about 1.0 mm-3.0 mm. In a specific embodiment length G' is about 2.0 mm. A length E' of the head 18 extending along the axial direction 36 from the neck 22 to the end 20 ranges from about 10 mm-15 mm. In a specific embodiment length E' is about 12.50 mm, such as 12.48 mm.

Still referring to FIG. 5, in an embodiment a radius J' from the axis 36 to inner wall 34 of the base 12 ranges from about 3.0 mm-4.5 mm. In a specific embodiment J' is 3.80 mm. In a specific embodiment, a radius K' from the longitudinal axis 36 to outer wall 32 of the base 12 is about 5 mm. It should be appreciated that the radii of the various features from the axis 36 to the inner and outer walls of the respective feature will be dependent upon a wall thickness of the respective feature and overall diameter of the balloon 10. The dimensions of the balloon 10 described with reference to FIG. 5 are applicable to the embodiments of the balloon 10 shown in FIGS. 1-4.

In the embodiments shown in the Figures the cylinder 16, base 12, resistance band 26, groove 24, neck 22, head 18 and end 20 are unitary with one another. However, in some embodiments the cylinder 16, base 12, resistance band 26, groove 24, neck 22, head 18 and end 20 are not unitary with one another.

When the balloon 10 is inflated, such as when the balloon 10 is used to stretch the foreskin of a patient, a fluid is passed through spigot 14, through the base 12 and into an interior space of the balloon 10. The fluid is generally air but may optionally be a liquid. Because the head 18 has the thinnest wall thickness out of the cylinder 16, base 12 and neck 22, the head has the greatest ability to stretch (e.g. elasticity) which means that the head 18 is the first region of the balloon 10 to expand. Further, the wall thickness of the neck 22 is chosen so that the neck 22 does not expand, or only minimally expands, when the balloon 10 is inflated. The wall thickness of the cylinder 16 (e.g. groove 24 and base 12) is also selected so that during inflation of the balloon 10 the cylinder 16 does not expand, that is, a diameter of the cylinder 16 remains substantially unchanged. See, for example, FIGS. 1 and 2, where in the inflated state (FIG. 2), a diameter of the outer face 32 of the cylinder 16 including neck 22 remains substantially unchanged compared to the neck 22 in a deflated state (FIG. 1). An advantage of the balloon 10 is that the head region 18 preferentially expands compared to the cylinder 16 (i.e. body), and this means that for small and delicate orifices the head 18 is less likely to slide out from the orifice. Put another way, the wall thickness of the neck 22 and cylinder 16 relative the wall thickness of the head 18 helps to keep fluid at the head (i.e. the distal end) of the balloon 10 in an inflated state.

For example, for current balloons used to dilate and stretch foreskin, there is no preferential expansion built into the balloon and the shaft and head expand proportionally with one another. A result of this is that for foreskins that are sufficiently tight, the head of the balloon is not able to expand and instead the shaft expands in preference to the head. This results in the shaft applying pressure on an outside of the foreskin which causes the head to withdraw from under the foreskin. This makes it difficult to reproducibly treat patients. Since the cylinder 16, including neck 22, does not expand during inflation, the cylinder 16 (i.e. body) is unlikely to apply a withdrawing pressure to the foreskin which helps to maintain the head 18 of the balloon 10 under the foreskin. Therefore, an embodiment of the balloon 10 helps to reduce the occurrence of the head withdrawing from an orifice in use.

It should be appreciated that the neck 22 and cylinder 16 may expand slightly during inflation, thereby increasing their respective diameters, but such expansion is minimal i.e. a diameter of the neck 22 and cylinder 16 may expand by <10%. In an embodiment, the head 18 expands by up to 100% of its deflated state. For example, in embodiments where the head 18 in a deflated state has a diameter of about 12 mm and the neck 22 has a diameter of about 10 mm, the head 18 in the inflated state may expand to have a diameter of up to 24 mm, such as 18 mm, and a diameter of the neck 22 may remain relatively unchanged such as 10.5 mm. In an embodiment the head 18 has an outer diameter in a deflated state ranging from about 6 mm to about 18 mm. In an embodiment, the cylinder 16 has an outer diameter in a deflated state ranging from about 8 mm to about 12 mm. In some embodiments the outer diameter of the cylinder 16 in the deflated state remains unchanged regardless of the diameter of the head 18 in the deflated state. In some embodiments the neck 22 expands relative the base 12, and the head 18 expands relative the neck 22.

A longitudinal length of the balloon 10 extends in a direction extending from the base 12 to the end 20, as depicted as dashed line 36. In an embodiment, the head 18 occupies approximately 20%-30% of the length of the balloon 10. In an embodiment the neck 22 is positioned approximately 60%-75% of the distance from the base 12 to the end 20. In an embodiment, a length of the balloon 10 ranges from about 30 mm to about 50 mm. In an embodiment, the head extends from about 10 mm to about 25 mm from the end 20 towards the base 12. In an embodiment, a distance from the base 12 to the neck 22 ranges from about 20 mm to about 30 mm.

In the embodiments shown in the Figures the end 20 of the head 18 has a wall thickness that is greater than the sidewall portion 19. Similar to the neck 22, the end 20 functions to limit the expansion of the balloon 10 in a region near the end 20. Limiting the expansion of the end 20 helps to ensure that the head 18 expands in a radial direction rather than in a longitudinal direction of the balloon 10 (e.g. in a direction along line 36 extending away from the base 12). In some embodiments, an overall length of the balloon 10 remains substantially unchanged (i.e. <15% change) between a deflated and inflated state.

The balloon 10 is made from a resiliently deformable material. In an embodiment, the balloon 10 is formed from a material that allows the balloon 10 to be self-supporting such that in a deflated state the balloon 10 does not collapse in on itself, as depicted in FIG. 1. In an embodiment the balloon is formed from a silicone-based material. For example, the balloon may be formed from a silicone rubber made from a SILPURAN® 6000/40 liquid silicone rubber precursor. In an embodiment the balloon is formed from a polymeric material such as rubber.

The balloon 10 is used to dilate and stretch an orifice such as that formed by a foreskin. To stretch a foreskin, the head 18 of the balloon 18 is first inserted underneath the foreskin. Generally, the end 20 is positioned to be at or near the head of the penis. In an embodiment, an insertion implement, such as a rod, is used to push the head 18 under the foreskin. The insertion implement can be inserted into an interior of the balloon 10 to help push the head 18 underneath the foreskin. As the balloon 10 can be self-supporting, this can help with inserting the balloon 10 and maintaining the balloon 10 under the foreskin.

Figure 6:
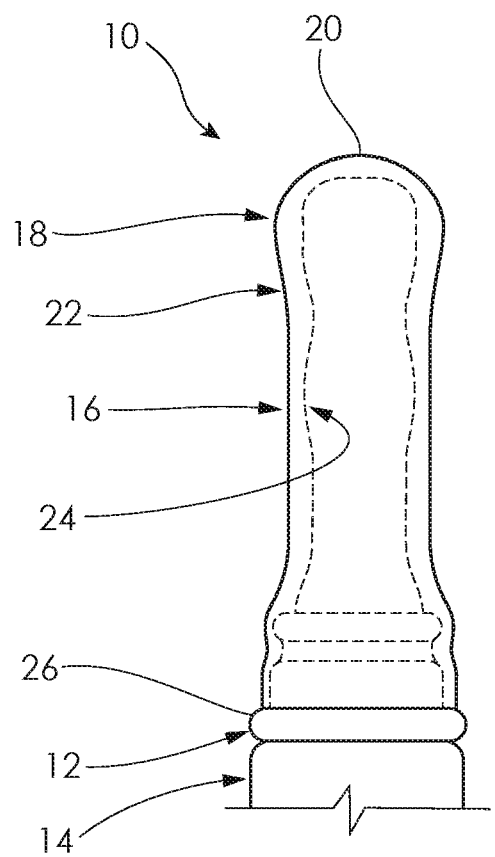
FIG. 6 shows a side view of an embodiment of a balloon of the disclosure in a deflated state when mounted on a spigot.

The balloon 10 is inflated once the balloon 10 positioned under the foreskin. To inflate the balloon 10 an inflation device is connected to the base 12 and a fluid is passed into the balloon 10. The spigot 14 forms part of an inflation device. An example of an inflation device includes a syringe or a squeeze bulb. In some forms the inflation device has a flow regulator, such as a tap or valve, that can be used to regulate a flow of fluid into and out of the balloon 10. The valve may be a one-way valve. The flow regulator is operable to maintain the balloon 10 in an inflated (expanded) state. In the embodiments of FIGS. 1 and 2 the auxiliary ring 28 is placed over balloon 10 to secure the balloon 10 to the spigot 14. However, the auxiliary ring 28 is not required in all embodiments, as shown in FIG. 6.

In some embodiments, a kit is provided which comprises the balloon 10 and a container that houses the balloon 10. In some embodiments, a kit is provided which comprises the system that comprises the balloon 10, and a container which houses the system. The container may be made from cardboard and/or plastic. The container may contain recesses to house the balloon 10 and/or system. For example, a container can contain a first recess to hold a plurality of balloons 10, and a second recess to hold the system.

Figure 7:
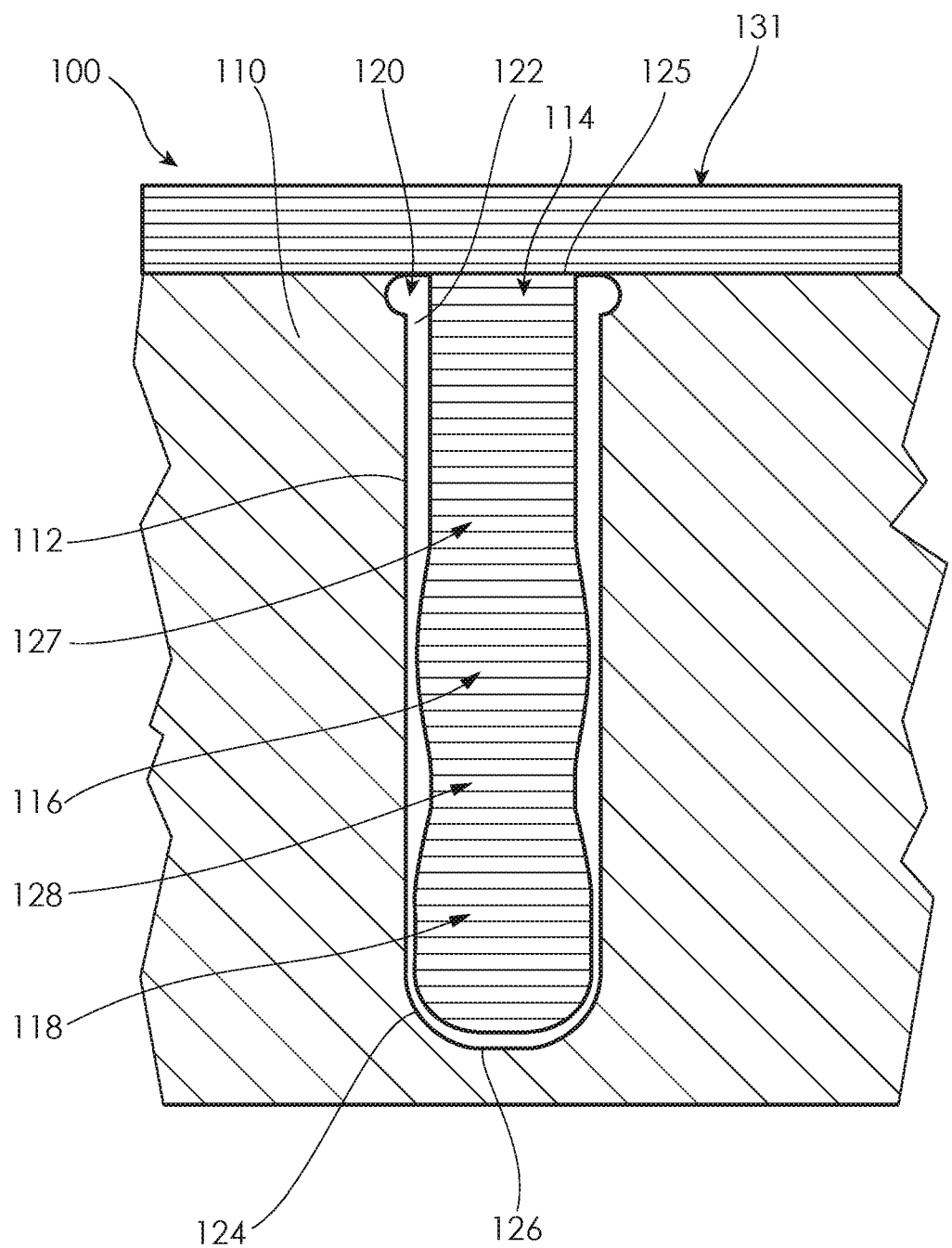
FIG. 7 shows a cross-section of a mould that is used to form an embodiment of a balloon.

Referring now to FIG. 7, a mould 100 is shown that is used to form the balloon 10. The mould 100 has a first component in the form of a female component 110. Female component 110 has a cavity 120. In an embodiment, the cavity 120 is defined by an elongate blind bore having an approximately constant diameter and a rounded base. An upper region of the cavity 120 is defined by cavity side wall 112. Extending from the cavity side wall 112 is a curved wall 124. An end of the cavity 120 is defined by a base wall 126. The base wall 126 extends from the curved wall 124. The cavity side wall 112, curved wall 124 and base wall 126 are collectively termed the cavity wall. The cavity wall defines an outer surface of the balloon 10. In an embodiment the female component 110 is formed from Calmax tool steel.

Mould 100 has a second component in the form of a male component, which in FIG. 7 is shown as spigot 114. Spigot 114 has a base 125 which extends from a base block 131. Base block 131 engaged with the female mould 110 to limit movement of the spigot 114 into the cavity 120. Extending from the base 125 is a first spigot region in the form of base region 127 for forming the base 12 and cylinder 16 of the balloon 10. A second spigot region in the form of head region 118 extends from the base region 127. The head region 118 is used to define the head 18 of the balloon 10. A diameter of the base region 127 is less than a diameter of the head region 118. Positioned between the base region 127 and head region 118 is a intermediate region 116 that is used to define the groove 24 of the balloon 10. A diameter of the intermediate region 116 can be the same or less than the diameter of the head region 118, but the diameter of the intermediate region 116 is greater than the diameter of the base region 127.

In the embodiment of FIG. 7, the neck 22 is formed around a neck region 128 that is positioned between the intermediate region 116 and head region 118. In embodiments of the mould 100 that do not have the intermediate region 116, the neck 22 is defined by the transition from the base region 127 to the head region 118. In an embodiment the spigot 114 is formed from 7000 Series aluminium.

The dimensions of features of the balloon 10 described with reference to FIG. 5, such as wall thickness, length, and diameter, are at least in part defined by the dimensions of the cavity 120, base region 127, head region 118, intermediate region 116 and neck region 128. Adjusting the dimensions of the cavity 120, base region 127, head region 118, intermediate region 116 and/or neck region 128 spigot will adjust the dimensions of the respective feature of a balloon 10. For example, decreasing a diameter of the base region 127 whilst maintaining a diameter of the cavity 120 will increase a wall thickness of the cylinder 16.

In an embodiment, the spigot 114 is formed from two or more components that are connectable with one another. Forming the spigot from two or more components can help in the removal of a balloon from the mould. In an embodiment, the base region 127, intermediate region 116 and optionally the neck region 128 is defined by a first spigot component and the head region 118 and optionally the neck region 128 is defined by a second spigot component that is connectable with the first spigot component. In an embodiment, the neck region is positioned on the first spigot component, the second spigot component. The neck region 128 may be defined when the first spigot component and the second spigot component are connected to one another.

In use, the spigot 114 is inserted into the cavity 120. An annulus 122 formed between the cavity wall and an outer surface of the spigot defines a volume that is filled with a balloon precursor material that is cured to form the balloon. In an embodiment, the balloon precursor material is SIL-PURAN® 6000/40 liquid silicone rubber precursor. Once the balloon 10 is formed, the spigot 114 is removed from the cavity 120 and then the balloon 10 is removed from the spigot 114. In an embodiment, following the formation of the balloon 10, the balloon is post-cured. Post curing can be at an elevated temperature, such as about 200° C. However, post-curing is not required in all embodiments. A suitable release agent is used to allow the balloon 10 to be released from the mould 100.

Figure 8:
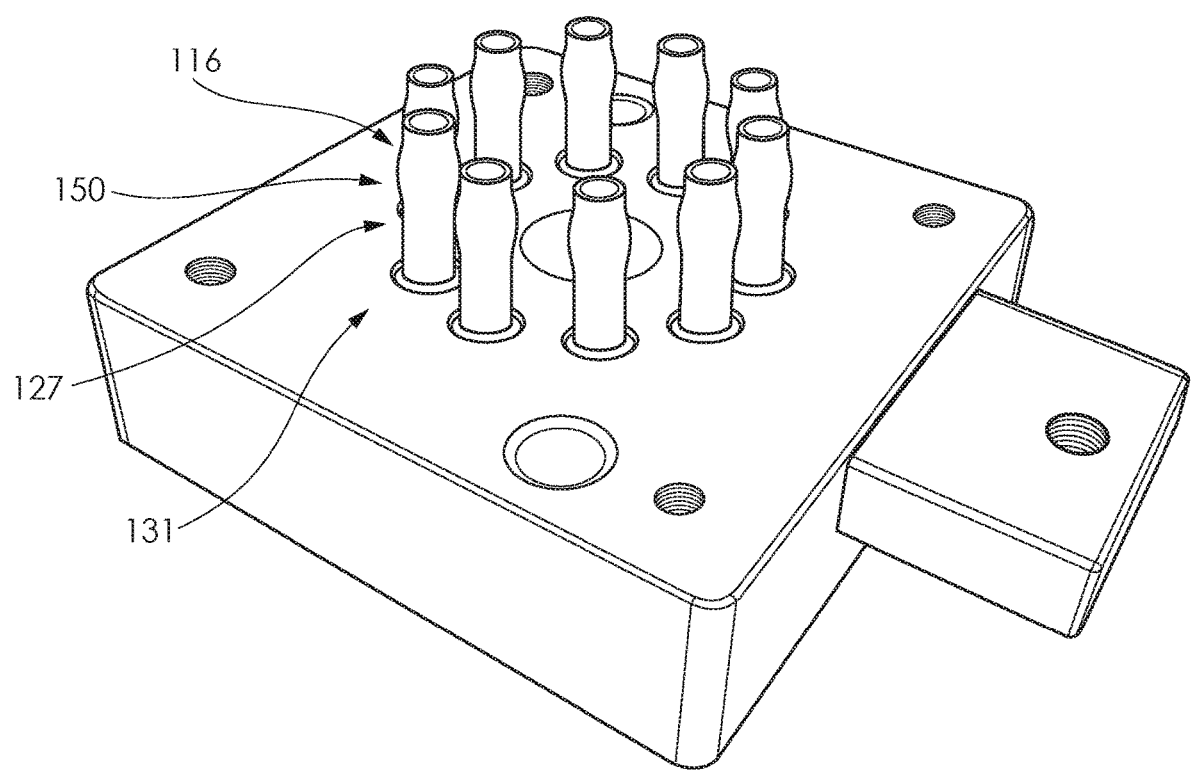
FIG. 8 shows a male mould component that is used to form an embodiment of a balloon.

An embodiment of a spigot is shown in FIG. 8 (multiple spigots are shown in FIG. 8). The spigot 150 has base region 127 and intermediate region 116. The spigot 150 extends from a base block 131. In FIG. 8, the base block 131 has a plurality of spigots 150 located thereat. A female component that is used to form the mould 100 is provided with a respective number of cavities to accommodate each spigot of the plurality of spigots 150.

Although specific embodiments of the balloon 10 have been described with reference to stretching a foreskin, the balloon of the current disclosure is not limited to use for stretching and dilating foreskin and can be used for dilating and stretching other orifices such as an ear canal, nasal passage, sinus, anus and vagina.

Further, the embodiments of the balloon described above have been designed for specific use for stretching a foreskin. However, for use with other orifices, other features of the balloon 10, such as a portion of the cylinder 16, may expand similarly or more than the head 18 in use. For example, in some embodiments, the balloon in an expanded shape may adopt a "dog bone" shape, with two expanded portions being axially spaced from one another.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure may be identified herein as preferred or particularly advantageous, it is contemplated that the present disclosure is not necessarily limited to these aspects.

In the claims which follow and in the preceding description, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments.

The invention claimed is:

1. A balloon configured for expanding a foreskin, the balloon comprising:
    a hollow body having a head and a neck, the neck having a length and the body being closed at a distal end and open at a proximal end with a longitudinal axis extending therebetween, the body having an inner face and an outer face defining a wall thickness of the body, the head extending from the neck and terminating at the closed distal end, the closed distal end defined by a transverse end wall being that portion of the head which extends across the distal end of the body in a direction transverse to the longitudinal axis, the head having a sidewall portion being that portion of the head which is directly connected to extend between each of the transverse end wall and the neck;
    wherein a wall thickness of the neck is greater than a wall thickness of the sidewall portion of the head, and a wall thickness of the transverse end wall is greater than a wall thickness of the sidewall portion of the head, such that when the balloon is inflated the head expands in a radial direction greater than in a direction of the longitudinal axis and a diameter of an outer face of the neck remains approximately constant over the length of the neck during inflation, to thereby form the balloon with a bulbous mushroom shape, the bulbous mushroom head having an outer diameter greater than an outer diameter of the neck, the outer diameter of the neck being substantially cylindrical.

2. The balloon as claimed in claim 1, wherein a length of the balloon extending along the direction of the longitudinal axis remains approximately constant during inflation.

3. The balloon as claimed in claim 1, wherein a first end of the neck comprises a peripheral lip that protrudes outwardly therefrom.

4. The balloon as claimed in claim 1, wherein the neck comprises a waist intermediate a first end and a second end of the neck.

5. The balloon as claimed in claim 4, wherein a wall thickness of the waist is less than a wall thickness of a remainder of the neck.

6. The balloon as claimed in claim 4, wherein the waist is formed as a progressive narrowing of a wall thickness of a section of the neck.

7. The balloon as claimed in claim 1, wherein the external diameter of the neck ranges from about 5 mm to about 15 mm.

8. The balloon as claimed in claim 1, wherein the head has a diameter within a range from about 6 mm to about 18 mm in a deflated state.

9. The balloon as claimed in claim 1, wherein the opening at the proximal end has a diameter within a range from about 5 mm to about 10 mm.

10. The balloon as claimed in claim 1, wherein the balloon is formed from silicone.

11. The balloon as claimed in claim 10, wherein the balloon is formed from a liquid silicone rubber precursor.

12. The balloon as claimed in claim 1, wherein the body and head are unitary with one another.

13. The balloon as claimed in claim 1, being self-supporting such that in a deflated state the balloon does not collapse in on itself.

14. The balloon as claimed in claim 9, wherein the opening at the proximal end has a diameter of 8 mm.

15. The balloon as claimed in claim 1, wherein the wall thickness of the neck is within a range from 1.0 mm-2.0 mm, the wall thickness of the sidewall portion of the head is within a range from 0.2 mm-0.6 mm and the wall is thickness of the transverse end wall is within a range from 0.7 mm-1.1 mm.

* * * * *